United States Patent [19]

Takano

[11] Patent Number: 5,090,414

[45] Date of Patent: Feb. 25, 1992

[54] INTRACAVITARY ULTRASOUND PROBE

[75] Inventor: Masayuki Takano, Ootawara, Japan

[73] Assignee: Kabushiki Kaisha Toshiba, Tokyo, Japan

[21] Appl. No.: 396,245

[22] Filed: Aug. 21, 1989

[30] Foreign Application Priority Data

Aug. 22, 1988 [JP] Japan .................. 63-206403

[51] Int. Cl.⁵ .............................................. A61B 8/00
[52] U.S. Cl. ........................ 128/662.05; 128/662.06; 128/660.1
[58] Field of Search .............. 128/660.09, 660.1, 662.04–662.06; 73/633

[56] References Cited

U.S. PATENT DOCUMENTS

| 4,330,874 | 5/1982 | Sorwick | 128/660.1 X |
| 4,494,548 | 1/1985 | Buon et al. | 128/660.1 |
| 4,742,829 | 5/1988 | Law et al. | 128/662.05 |
| 4,756,313 | 7/1988 | Terwilliger | 128/662.06 X |
| 4,763,662 | 8/1988 | Yokoi | 128/662.06 X |
| 4,911,173 | 3/1990 | Terwilliger | 128/662.06 |
| 4,928,699 | 5/1990 | Sasai | 128/662.06 |

Primary Examiner—Francis Jaworski
Attorney, Agent, or Firm—Cushman, Darby & Cushman

[57] ABSTRACT

An intracavitary ultrasound probe comprises a rotating shaft rotatably supported inside an elongated body and adapted to swing or rotate a transducer element, an motor housed in a handle, and a stab needle guide extending in substantially parallel to the elongated body. The motor is arranged in a manner to be offset from the rotating shaft, and the ultrasound probe further comprises a mechanism for transmitting torque from the motor to the rotating shaft. Since, therefore, the handle is offset from the elongated body, a wide space for operating a stab needle is provided, thus ensuring easy operation of the stab needle. In addition, a wide space for employing a syringe is also provided. As a result of this structure, the patient's pain is reduced, and the probe is easy to rotate or tilt.

10 Claims, 3 Drawing Sheets

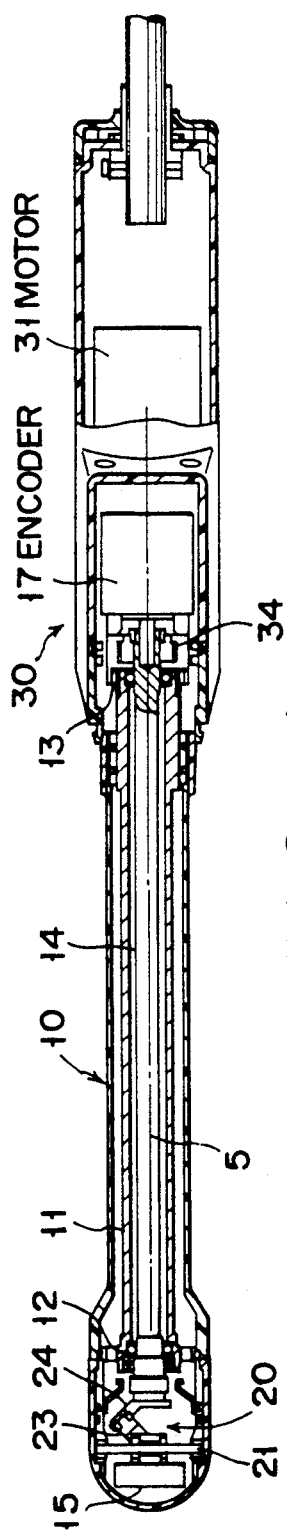
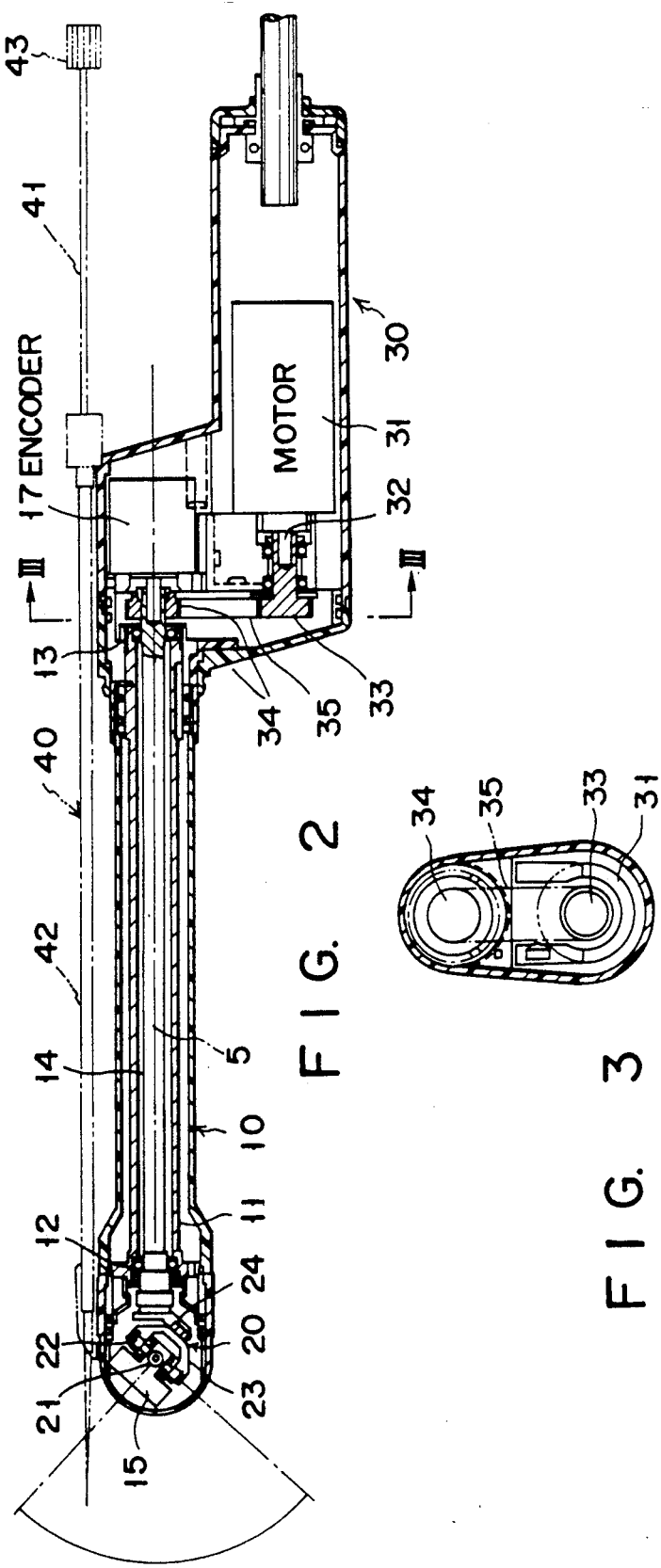

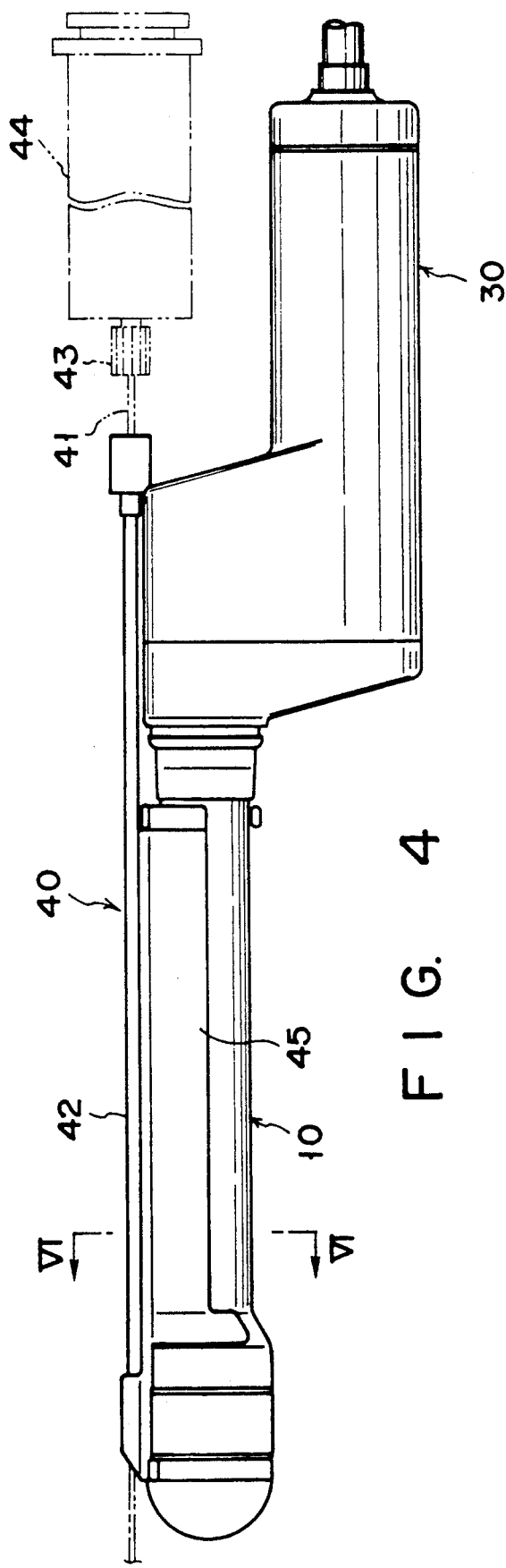
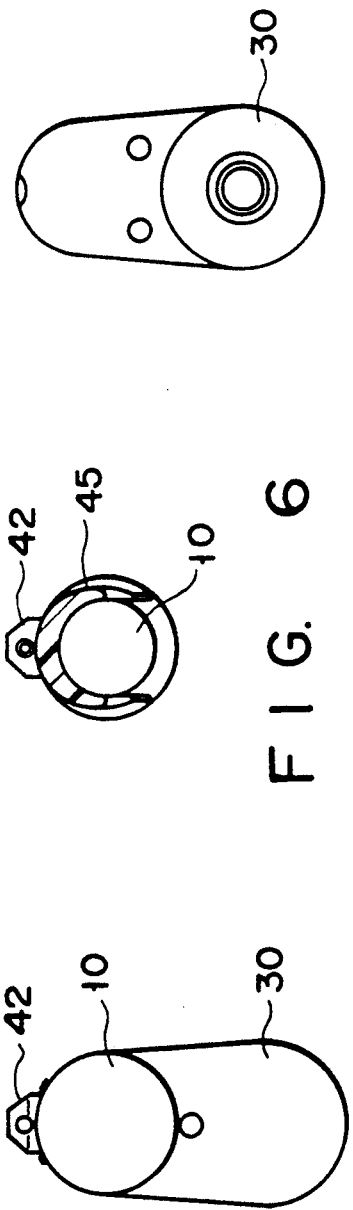
FIG. 4
FIG. 5
FIG. 6
FIG. 7

INTRACAVITARY ULTRASOUND PROBE

BACKGROUND OF THE INVENTION

1. Field of the Invention

The present invention relates to an intracavitary ultrasound probe of a mechanical scan type, which is inserted into a body cavity and scans an internal organ to obtain a tomographic image thereof by transmitting and receiving ultrasound beams with reference to the internal organ, and which is equipped with a stab needle assembly (or a biopsy needle assembly).

2. Description of the Related Art

Intracavitary ultrasound probes are primarily employed in the fields of gynecology and obstetrics for the purpose of transvaginally examining intrapelvic organs, such as the vagina, the uterus, and the ovaries.

Such probes fall into two categories, namely the electronic scan type and the mechanical scan type. The construction of a mechanical scan type probe will now be described.

The mechanical scan type probe comprises an elongated body having a transducer element at the distal end and adapted for insertion into the vagina, and a handle extending from the proximal end of the elongated body in a manner to be substantially coaxial with the elongated body. A rotating shaft is rotatably supported within the body, and the distal end of this rotating shaft is mechanically coupled to the transducer element. A motor is housed in the handle, and the driving shaft of this motor is coaxially coupled to the proximal end of the rotating shaft.

With the above construction, when the motor is driven, with the elongated body inserted in the vagina, the rotating shaft is rotated and the transducer element swings or rotates. Simultaneously, the transducer element transmits ultrasound beams to the intrapelvic organs and receives the ultrasound beams reflected from them. As a result, the intrapelvic organs are sector scanned (or radially-scanned) with the ultrasound beams, and an ultrasonic tomogram of the intrapelvic organs is displayed on a monitor.

In some cases, a stab needle assembly is fitted to the intracavitary ultrasound probe, mainly for removing an ovum from the ovary. The stab needle assembly comprises an elongated, hollow stab needle (which is like the needle of an injector), and a stab needle guide which is coupled to the elongated body of the probe and extends in parallel thereto for the guiding of the stable needle. A syringe for sucking an ovum is coupled to the proximal end of the stab needle.

The stab needle assembly is used, e.g., for a sterile woman whose oviduct connecting the uterus to the ovaries is clogged. That is, it is used for removing an ovum from the ovary, for extracorporeal fertilization, and for returning the fertilized ovum to the ovary. More specifically, the operator inserts a probe equipped with the stab needle assembly into the vagina while holding the handle of the probe. The ovary or the like is scanned with ultrasound beams, and an ultrasound tomographic image of the ovary or the like is displayed on a monitor. While observing the tomographic image on the monitor, the operator inserts the tip end of the stab needle into the ovary. By producing suction by use of the syringe coupled to the proximal end of the stab needle, the ovum is removed from the ovary and sucked into the syringe. After the ovum is fertilized extracporeally, it is returned to the ovary by following similar procedures.

In some cases, the stab needle assembly is used for removing a tissue of a tumor which may grow in the vagina, so as to judge whether or not the tumor is malignant.

In the case of the conventional probe, the elongated body and the handle are substantially coaxial, and the stab needle guide extends in parallel to the elongated body. Since, therefore, the proximal end of the stab needle and the handle are located close to each other, the region around the proximal end of the stab needle does not provide a sufficiently wide space needed for reliably operation of the stab needle. In addition, a syringe cannot be easily attached to the proximal end of the stab needle.

Conventionally, these problems have been solved by attaching the stab needle guide slantwise with reference to the elongated body. With this construction, a sufficiently wide space is provided between the handle and the proximal end of the stab needle, so that it is possible both to reliably operate the stab needle and to easily attach the syringe to the proximal end of the stab needle. However, this construction is disadvantageous, in that the distance between the proximal end of the stab needle guide and that of the elongated body is comparatively long. Therefore, when the stab needle assembly and the probe are inserted into the vagina of the patient, the proximal end of the stab needle guide is pressed against the vaginal wall, causing pain to the patient.

During the examination, the operator may feel it necessary to rotate the scan plane, so as to obtain tomographic images in various directions. For this purpose, the operator tries to rotate the probe around its longitudinal axis, but this cannot be easily done if the proximal end of the stab needle guide is pressed against the vaginal wall. In addition, the patient suffers much pain when the probe is being rotated by the operator.

The operator may also feel it necessary to tilt the scan plane, so as to obtain various tomographic images. For this purpose, the operator tries to tilt the probe in a manner to move the distal end of the probe. However, the tilting angle is limited if the proximal end of the stab needle guide is pressed against the vaginal wall, and the patient suffers much pain in this case as well.

SUMMARY OF THE INVENTION

Accordingly, an object of the present invention is to provide a intracavitary ultrasound probe of a mechanical scan type, which ensures a wide space needed for easy operation of the stab needle, and which can be easily rotated or tilted without giving much pain to the patient.

According to the present invention, there is provided an intracavitary ultrasound probe, comprising:

an elongated body including a distal end, a proximal end, and a rotating shaft;

a transducer element for scanning an object to be examined with ultrasound beams, the transducer element being located at the distal end of the elongated body and movable in response to torque transmitted from the rotating shaft;

a stab needle guide for guiding a stab needle, the stab needle guide being coupled to the elongated body and extending substantially in parallel to the elongated body;

a driving source located at the proximal end of the elongated body in a manner to be offset from the rotating shaft;

means for transmitting the torque from the driving source to the rotating shaft; and a handle which incorporates the driving source therein, so that the handle is offset from the elongated body.

In the intracavitary ultrasound probe of the present invention, the driving source is so located as to be offset from the rotating shaft, so that the handle is offset from the elongated body. With this construction, a wide stab needle-operating space is provided between the stab needle and the handle, thus ensuring reliable operation of the stab needle. Moreover, a syringe can be easily coupled to the stab needle since a sufficiently wide space for this purpose is provided in the vicinity of the proximal end of the stab needle.

In the intracavitary ultrasound probe of the present invention, the stab needle guide extends substantially i parallel to the elongated body and is coupled thereto. Therefore, it is not likely that the stab needle guide will press the vaginal wall of a patient. As a result, the patient's pain during examination can be reduced, and the operator can easily rotate or tilt the probe. In addition, the tilting angle of the probe is free from restriction.

In the conventional probe, the elongated body and the handle are substantially coaxial and have a substantially circular cross section. Since this construction does not permit the operator to recognize how the scan plane is positioned relative to the handle, a small projection is formed on the handle as a sign for indicating the position of the scan plane. However, it is difficult for the operator to recognize the sign by merely looking at it, so that it is not always possible for the operator to correctly judge the position of the scan plane.

In the present invention, in contrast, the handle is offset from the elongated body. Therefore, the position of the scan plane and the direction in which the handle is offset from the elongated body have a certain relationship. It is therefore possible for the operator to easily recognize the position of the scan plane by merely glancing at the exterior of the probe.

BRIEF DESCRIPTION OF THE DRAWINGS

FIG. 1 shows a horizontally-taken section of an intracavitary ultrasound probe according to the first embodiment of the present invention;

FIG. 2 shows a vertically-taken section of the probe shown in FIG. 1;

FIG. 3 shows a cross section taken along line III—III in FIG. 2;

FIG. 4 is a front view of the probe shown in FIG. 1;

FIG. 5 is a left side view of the probe shown in FIG. 3;

FIG. 6 shows a cross section taken along line VI—VI in FIG. 4;

FIG. 7 is a right side view of the probe shown in FIG. 3; and

DETAILED DESCRIPTION OF THE PREFERRED EMBODIMENTS

Figure 8:
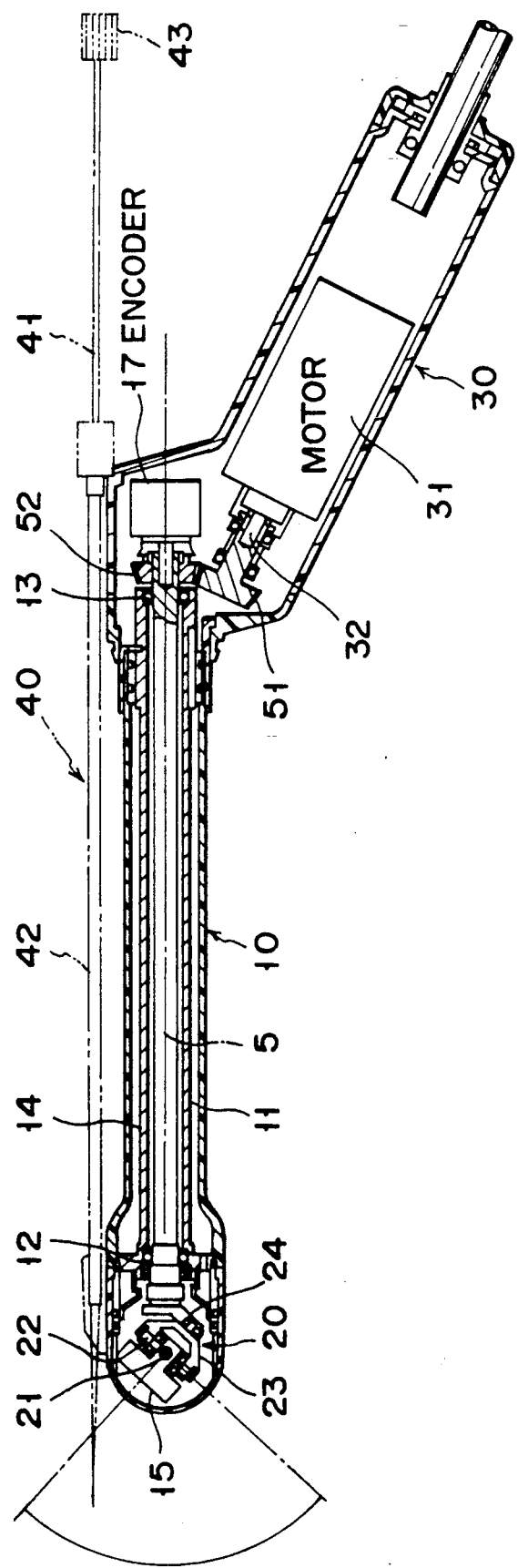
FIG. 8 shows a vertically-taken section of a intracavitary ultrasound probe according to the second embodiment of the present invention.

FIGS. 1 through 7 illustrate an intracavitary ultrasound probe according to the first embodiment of the present invention. This probe is comprised mainly of elongated body 1 adapted for insertion into the vagina of a patient, and handle 30 extending from the proximal end of elongated body 10.

Elongated body 10 is made of resin pipe and has the longitudinal or central axis indicated by reference numeral 5. Cylindrical holding member 11 is housed inside elongated body 10. Bearings 12 and 13 ar attached to the distal and proximal ends of holding member 11, respectively. Rotating shaft 14 extending along central axis 5 is rotatably supported by bearings 12 and 13. Transducer element 15 is arranged at the distal end of elongated body 10. This transducer element is mechanically coupled to the distal end of rotating shaft 14 by link mechanism 20, and is rotatably supported by means of fixing shaft 21. Shaft 22, fixed to transducer element 15, is rotatably supported at the ends of U-shaped arm 23. The central portion of the U-shaped arm is rotatably supported by member 24, which is secured to rotating shaft 14. Therefore, when member 24 is rotated by rotating shaft 14, arm 22 performs precession, thus swinging transducer element 15. Simultaneous with this swinging motion, transducer element 15 transmits ultrasound beams toward the intrapelvic organs and receives the ultrasound beams reflected from them. As a result, the intrapelvic organs are sector-scanned with the ultrasound beams, and an ultrasonic tomographic image thus obtained is displayed on a monitor (not shown).

Motor 31 is arranged inside handle 30 in a manner to be offset from rotating shaft 14. More specifically, driving shaft 32 of motor 31 does not extend coaxially with respect to central axis but in parallel thereto. Likewise, handle 30 does not extend coaxially with respect to central axis 5 but in parallel thereto. With this construction, a wide space for operating stab needle 41 is provided between handle 30 and stab needle 41, as will be detailed later.

Driving pulley 33 is attached to driving shaft 32 of motor 31, and driven pulley 34 is attached to the proximal end of rotating shaft 14. Timing belt 35 is wound around pulleys 33 and 34. In the first embodiment, pulleys 33 and 34 and belt 35 constitute a torque transmitting means. Therefore, when motor 31 is driven, its torque is transmitted to rotating shaft 14 via driving pulley 33, timing belt 35, and driven pulley 34. As a result, transducer element 15 swings.

Encoder 17 is coupled to the proximal end of rotating shaft 14. This encoder detects the swinging angle of transducer element 15 on the basis of the relationship which that swinging angle has with respect to the angle of rotation of shaft 14. The swinging angle of transducer element 15 determines the direction in which one ultrasound beam is transmitted and received, and an ultrasound tomographic image is displayed in correspondence to the swinging angle. In the present invention, encoder 17 is coupled directly to the proximal end of rotating shaft 14. With this construction, it is not likely that the swinging angle detected by encoder 14 will include an error due to backslash or slippage. Therefore, a tomographic image can be displayed on the monitor without being shifted from the right position.

Stab needle assembly 40 (which is also referred to as a biopsy needle assembly) is attached to the probe in a detachable fashion. Stab needle assembly 40 comprises hollow stab needle 41 (which looks like long needle of an injector), and stab needle guide 42 extending parallel to central axis 5 of elongated body 10 and adapted for guiding stab needle 41 therethrough. As is shown in FIG. 4, connector 43 to which syringe 44 is to be coupled is provided at the proximal end of stab needle 41. Stab needle guide 42 includes clamp member 45 which is elastically deformable in a manner to be held by elongated body 40. By means of this clamp member, stab needle guide 42 can be attached to elongated body 10 in a detachable fashion.

The stab needle assembly is used, e.g., for a sterile woman. In other words, it is used for removing an ovum from the ovary, for extracorporeal fertilization, and for returning the fertilized ovum to the ovary. More specifically, the operator inserts the probe equipped with the stab needle assembly into the vagina while holding the handle of the probe. The ovary or the like is scanned with ultrasound beams, and an ultrasound tomographic image of the ovary or the like is displayed on the monitor. While observing the tomographic image on the monitor, the operator inserts the tip end of stab needle 41 into the ovary. By producing suction by use of syringe 44 coupled to the proximal end of stab needle 41, the ovum is removed from the ovary and sucked into syringe 44. After the ovum is fertilized extracorporeally, it is returned to the ovary by following similar procedures.

Since handle 30 is offset from elongated body 10, a wide space for operating stab needle 41 is provided between stab needle 41 and handle 30. Therefore, stab needle 41 is easy to operate when such a surgical operation as mentioned above is conducted. In addition, since a space required for the coupling of syringe 44 is also provided in the vicinity of the proximal end of stab needle 41, syringe 44 can be easily coupled to stab needle 41.

Stab needle guide 42 extends substantially in parallel to elongated body 10 and is coupled thereto. With this construction, it is unlikely that stab needle guide 42 will press the vaginal wall of a patient. As a result, the patient's pain during the surgical operation or examination is reduced, and the operator can easily rotate or tilt the probe. In addition, the tilting angle of the probe is free from restriction.

As mentioned above, the conventional probe has a small projection formed on the handle, and this projection serves as a sing for indicating how the scan plane is positioned relative to the handle. However, since it is difficult for the operator to recognize such a sing, it is not always possible for the operator to correctly judge the position of the scan plane. This problem is solved in the present invention by arranging handle 30 in a manner to be offset from elongated body 10. Since, therefore, the position of the scan plane has a certain relationship with the direction in which handle 30 is offset from elongated body 10, it is possible for the operator to easily recognize the position of the scan plane by merely glancing at the exterior of the probe.

FIG. 8 shows an intracavitary ultrasound probe according to the second embodiment of the present invention. The probe of the second embodiment is similar to that of the first embodiment, except that the means for transmitting torque from motor 31 to rotating shaft 14 is constituted by a pair of bevel gears, namely, driving bevel gear 51 attached to driving shaft 32 of motor 31, and driven bevel gear 52 attached to the proximal end of rotating shaft 14 and in mesh with driving bevel gear 51. When motor 31 is driven, bevel gears 51 and 52 are rotated, and rotating shaft 14 is therefore rotated. As a result, transducer element 15 swings.

Since the torque-transmitting means according to the second embodiment is constituted by a pair of bevel gears 51 and 52, driving shaft 32 of motor 31 can arranged slantwise with reference to rotating shaft 14. Therefore, handle 30 can be arranged slantwise with reference to elongated body 10. With this construction, a stab needle-operating space which is wider than that of the first embodiment is provided between stab needle 41 and handle 30. Accordingly, stab needle 41 is easier to operate.

The present invention is not limited to the above-mentioned embodiments. For example, the torque transmitting means may be constituted by spur gears, in place of the pulleys and timing belt, or of the bevel gears. Further, torque-transmitting means of various types may be employed for transmitting torque from the motor to the rotating shaft.

What is claimed is:

1. An intracavitary ultrasound probe, comprising:
   an elongated body including a distal end, a proximal end, and a rotatably-supported rotating shaft;
   a transducer element, located at the distal end of said elongated body, for scanning an object to be examined with ultrasound beams, said transducer element being movable in response to torque transmitted from the rotating shaft while simultaneously transmitting and receiving the ultrasound beams;
   a stab needle guide for guiding a stab needle, said stab needle guide being coupled to said elongated body and extending substantially in parallel to said elongated body;
   a driving source located at the proximal end of said elongated body, which is offset from the rotating shaft, said driving source including a driving shaft extending in a non coaxial manner with respect to the rotating shaft;
   means for transmitting the torque from said driving source to the rotating shaft, said transmitting means including:
   a first pulley coupled to said driving shaft;
   a second pulley coupled to a proximal end of the rotating shaft; and
   a belt would around the first and second pulleys;
   a handle which incorporates said driving source therein, so that said handle is offset from said elongated body; and
   an encoder, coupled directly to the proximal end of the rotating shaft, for detecting a swinging angle of said transducer element;
   wherein a space for operating said stab needle is provided between said stab needle and said handle and wherein said driving shaft is parallel to the rotating shaft, so that said handle is parallel to said elongated body.

2. An intracavitary ultrasound probe according to claim 1, further comprising a link mechanism for mechanically linking the distal end of the rotating shaft and said transducer element to each other, said link mechanism being adapted to swing said transducer element with the torque transmitted thereto from the rotating shaft, so that said transducer element sector-scans the object with the ultrasound beams.

3. An intracavitary ultrasound probe according to claim 1, wherein said stab needle includes a connector to which a syringe is to be coupled.

4. An intracavitary ultrasound probe according to claim 1, wherein said stab needle guide includes a clamp member which is elastically deformable in a manner to be held by said elongated body, so that said stab needle guide is attached to said elongated body in a detachable fashion.

5. An intracavitary ultrasound probe according to claim 1, wherein said elongated body houses the rotating shaft and includes a cylindrical support member for rotatably supporting the rotating shaft and includes a cylindrical support member for rotatably supporting the rotating shaft.

6. An intracavitary ultrasound probe, comprising:
an elongated body including a distal end, a proximal end, and a rotatably-supported rotating shaft;
a transducer element, located at the distal end of said elongated body, for scanning an object to be examined with ultrasound beams, said transducer element being movable in response to torque transmitted from the rotating shaft while simultaneously transmitting and receiving the ultrasound beams;
a stab needle guide for guiding a stab needle, said stab needle guide being coupled to said elongated body and extending substantially in parallel to said elongated body;
a driving source located at the proximal end of said elongated body, which is offset from the rotating shaft, said driving source including a driving shaft extending in a non coaxial manner with respect to the rotating shaft;
means for transmitting the torque from said driving source to the rotating shaft, said transmitting means including:
a first gear coupled to said driving shaft; and
a second gear coupled to the proximal end of the rotating shaft and in mesh with the first gear;

a handle which incorporates said driving source therein, so that said handle is offset from said elongated body; and
an encoder, coupled directly to the proximal end of the rotating shaft, for detecting a swinging angle of said transducer element;
wherein a space for operating said stab needle is provided between said stab needle and said handle and wherein said driving shaft is arranged slantwise with reference to the rotating shaft, so that said handle is arranged slantwise with reference to said elongated body.

7. An intracaviary ultrasound probe according to claim 6, further comprising a link mechanism for mechanically linking the distal end of the rotating shaft and said transducer element to each other, said link mechanism being adapted to swing said transducer element with the torque transmitted thereto from the rotating shaft, so that said transducer element sector-scans the object with the ultrasound beams.

8. An intracavitary ultrasound probe according to claim 6, wherein said stab needle includes a connector to which a syringe is to be coupled.

9. An intracavitary ultrasound probe according to claim 6, wherein said stab needle guide includes a clamp member which is elastically deformable in a manner to be held by said elongated body, so that said stab needle guide is attached to said elongated body in a detachable fashion.

10. An intracavitary ultrasound probe according to claim 6, wherein said elongated body houses the rotating shaft and includes a cylindrical support member for rotatably supporting the rotating shaft.

* * * * *